(12) United States Patent
Stevens-Wright

(10) Patent No.: US 7,686,802 B2
(45) Date of Patent: Mar. 30, 2010

(54) JUNCTION OF CATHETER TIP AND ELECTRODE

(75) Inventor: Debbie Stevens-Wright, Andover, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 698 days.

(21) Appl. No.: 10/551,289

(22) PCT Filed: Mar. 29, 2004

(86) PCT No.: PCT/US2004/009610

§ 371 (c)(1),
(2), (4) Date: Aug. 21, 2006

(87) PCT Pub. No.: WO2004/086992

PCT Pub. Date: Oct. 14, 2004

(65) Prior Publication Data

US 2007/0083191 A1    Apr. 12, 2007

Related U.S. Application Data

(60) Provisional application No. 60/458,489, filed on Mar. 28, 2003, provisional application No. 60/458,490, filed on Mar. 28, 2003, provisional application No. 60/458,491, filed on Mar. 28, 2003, provisional application No. 60/458,643, filed on Mar. 28, 2003, provisional application No. 60/458,856, filed on Mar. 28, 2003.

(51) Int. Cl.
*A61B 18/18*    (2006.01)

(52) U.S. Cl. .............................. 606/41; 606/32; 606/34; 600/374

(58) Field of Classification Search ............. 606/32–34, 606/41–42, 45–50; 604/114; 600/374
See application file for complete search history.

(56) References Cited

U.S. PATENT DOCUMENTS

| | | | | |
|---|---|---|---|---|
| 4,664,120 A | | 5/1987 | Hess | |
| 4,832,048 A | * | 5/1989 | Cohen | 606/41 |
| 4,896,671 A | * | 1/1990 | Cunningham et al. | 600/374 |
| 4,966,597 A | * | 10/1990 | Cosman | 606/50 |
| 5,098,431 A | | 3/1992 | Rydell | |
| 5,122,137 A | * | 6/1992 | Lennox | 606/40 |
| 5,230,349 A | * | 7/1993 | Langberg | 607/122 |
| 5,257,635 A | * | 11/1993 | Langberg | 607/122 |
| 5,348,554 A | * | 9/1994 | Imran et al. | 606/41 |

(Continued)

FOREIGN PATENT DOCUMENTS

EP    1 169 975 A1    1/2002

OTHER PUBLICATIONS

PCT International Search Report for International Application No. PCT/US2004/009610; Sep. 1, 2004.

*Primary Examiner*—Linda C Dvorak
*Assistant Examiner*—Amanda Scott
(74) *Attorney, Agent, or Firm*—Wolf, Greenfield & Sacks, P.C.

(57) ABSTRACT

Junctions of ablation electrodes and catheters are disclosed. Electrophysiology catheter systems include a recessed region such as a channel at a junction of an electrode and a catheter shaft. The channel can help to reduce electrode hotspots, energy density and/or blood coagulation at the junction. The channel may be incorporated in a distal tip electrode or a ring electrode.

36 Claims, 3 Drawing Sheets

U.S. PATENT DOCUMENTS

| | | |
|---|---|---|
| 5,716,389 A | 2/1998 | Walinsky et al. |
| 5,895,355 A * | 4/1999 | Schaer ..................... 600/381 |
| 5,906,614 A * | 5/1999 | Stern et al. ................ 606/42 |
| 6,030,382 A * | 2/2000 | Fleischman et al. ........... 606/41 |
| 6,048,329 A * | 4/2000 | Thompson et al. ....... 604/95.04 |
| 6,053,912 A * | 4/2000 | Panescu et al. ............... 606/40 |
| 6,056,745 A * | 5/2000 | Panescu et al. ............... 606/42 |
| 6,078,830 A * | 6/2000 | Levin et al. ................. 600/374 |
| 6,096,035 A * | 8/2000 | Sodhi et al. ................. 606/41 |
| 6,217,573 B1 * | 4/2001 | Webster ..................... 606/41 |
| 6,217,574 B1 * | 4/2001 | Webster ..................... 606/41 |
| 6,408,199 B1 | 6/2002 | Goldin |
| 6,511,478 B1 * | 1/2003 | Burnside et al. ............. 606/41 |
| 6,514,246 B1 * | 2/2003 | Swanson et al. ............. 606/41 |
| 6,522,930 B1 * | 2/2003 | Schaer et al. ............. 607/101 |
| 6,547,788 B1 * | 4/2003 | Maguire et al. .............. 606/41 |
| 6,569,162 B2 | 5/2003 | He |
| 6,939,350 B2 * | 9/2005 | Phan ......................... 606/49 |
| 6,955,173 B2 * | 10/2005 | Lesh ........................ 128/898 |
| 2003/0028185 A1 * | 2/2003 | He ............................. 606/41 |

* cited by examiner

JUNCTION OF CATHETER TIP AND ELECTRODE

RELATED APPLICATIONS

This application claims priority under 35 U.S.C. § 119(e) to U.S. Provisional Application Ser. No. 60/458,489, entitled "Electrode for Electrophysiology Catheter Having an Eccentric Surface", filed on Mar. 28, 2003, U.S. Provisional Application Ser. No. 60/458,490, entitled "Electrophysiology Catheter Allowing Adjustment Between Electrode and Tissue Gap", filed on Mar. 28, 2003, U.S. Provisional Application Ser. No. 60/458,491, entitled "Shape Shifting Electrode Geometry for Electrophysiology Catheters", filed on Mar. 28, 2003, U.S. Provisional Application Ser. No. 60/458,643, entitled "Method and Apparatus for Selecting Temperature/Power Set Points in Electrophysiology Procedures", filed on Mar. 28, 2003, and U.S. Provisional Application Ser. No. 60/458,856, entitled "Catheter Tip/Electrode Junction Design for Electrophysiology Catheters" filed on Mar. 28, 2003, all five of which are each incorporated herein by reference in their entireties.

BACKGROUND OF INVENTION

1. Field of Invention

The invention relates to medical devices and methods for performing ablation procedures. More particularly, the invention relates to methods and apparatus for limiting electrode heating and blood coagulation during ablation procedures.

2. Discussion of Related Art

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

Over time, the electrical impulses traveling through the heart can begin to travel in improper directions, thereby causing the heart chambers to contract at improper times. Such a condition is generally termed a cardiac arrhythmia, and can take many different forms. When the chambers contract at improper times, the amount of blood pumped by the heart decreases, which can result in premature death of the person.

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel (e.g. the femoral vein or artery) and into an endocardial site (e.g., the atrium or ventricle of the heart), and deliberately inducing an arrhythmia so that a continuous, simultaneous recording can be made with a multichannel recorder at each of several different endocardial positions. When an arrythormogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

Atrial fibrillation together with atrial flutter are the most common sustained arrhythmias found in clinical practice.

Another source of arrhythmias may be from reentrant circuits in the myocardium itself. Such circuits may not necessarily be associated with vessel ostia, but may be interrupted by means of ablating tissue either within the circuit or circumscribing the region of the circuit. It should be noted that a complete 'fence' around a circuit or tissue region is not always required in order to block the propagation of the arrhythmia; in many cases simply increasing the propagation path length for a signal may be sufficient. Conventional means for establishing such lesion 'fences' include a multiplicity of point-by-point lesions, dragging a single electrode across tissue while delivering energy, or creating an enormous lesion intended to inactivate a substantive volume of myocardial tissue.

In creating lesions, care is taken to limit blood coagulation and tissue charring and desiccation. These undesirable effects can occur if temperatures in the tissue or blood rise to 100° C. or higher. In addition to effects on the blood and tissue, temperatures of 100° C. or more at the electrode-tissue interface can foul an electrode due to tissue charring. Various strategies are employed to maintain temperatures below 100° C. Electrode cooling (active and/or passive) is one strategy employed in an attempt to cool the tissue at the tissue surface. Other strategies include limiting the power applied to the electrode based on pre-determined estimates of appropriate power levels, and reducing the power applied to the electrode in response to feedback signals from the electrode or other sensors. Reduced power application, however, is balanced with the desirability of raising the temperature of an adequate volume of tissue above its viability temperature and the benefits of reducing total procedure time.

Blood coagulation can occur when electrode hotspots lead to convective heating of the blood or the energy being emitted by the electrode is concentrated due to the geometry of the electrode arrangement. There exists a need to improve the delivery of energy to tissue to form lesions without exceeding electrode temperatures or energy concentrations that result in blood coagulation.

SUMMARY OF INVENTION

Embodiments of the present invention encompass apparatus and method for creating lesions in heart tissue (ablating) to create a region of necrotic tissue which serves to disable the propagation of errant electrical impulses caused by an arrhythmia. Embodiments of the present invention also encompass apparatus and methods for limiting blood coagulation during ablation procedures.

According to one embodiment, a catheter comprises a catheter shaft having an insulating material and a diameter, and an ablation electrode forming a junction with the shaft, the ablation electrode having an exposed surface. Extending from the junction, the exposed electrode surface has a first diameter portion with a first diameter that is smaller than the shaft diameter, the first diameter portion forming an angle with the insulating material. The exposed electrode surface has a second diameter portion with a second diameter that is larger than the first diameter of the first diameter portion, the second diameter portion having a largest diameter that is smaller than a length of the second diameter portion.

According to another embodiment, a catheter comprises a shaft including an electrically insulating material, and an ablation electrode forming a junction with the insulating material and having an exposed surface that forms a channel with the insulating material. A base of the channel is the exposed electrode surface of a first diameter portion of the electrode, a first sidewall of the channel is the insulating material, a second sidewall of the channel is the exposed electrode surface of a second diameter portion of the electrode, and a length of the second diameter portion of the electrode is greater than a diameter of the second diameter portion.

According to a further embodiment, a catheter comprises a catheter having an insulating sheath, and an ablation electrode non-moveably attached to the insulating sheath, forming a junction with the insulating sheath, and having an exposed surface that forms a channel with the insulating sheath. A base of the channel is the exposed electrode surface, a first sidewall of the channel is the insulating sheath, a second sidewall of the channel is the exposed electrode surface, and a width of the base of channel is at least one-tenth of the size of the largest diameter of the electrode and less than the smallest diameter of the electrode.

According to another embodiment, a method of manufacturing a catheter tip comprises providing a catheter shaft with an insulating sheath, providing an ablation electrode having a first diameter portion with an exposed surface and a second diameter portion with an exposed surface, the first and second diameter portions forming a transition face, and the second diameter portion having a length that is larger than a largest diameter of the second diameter portion. The method further comprises attaching the electrode to the shaft, wherein the transition face and the sheath form sidewalls of a channel and the first diameter portion of the electrode forms a base of the channel.

BRIEF DESCRIPTION OF DRAWINGS

The accompanying drawings are not intended to be drawn to scale. In the drawings, like components that are illustrated in various figures are represented by a like numeral. For purposes of clarity, not every component may be labeled in every drawing. In the drawings.

DETAILED DESCRIPTION

Figure 1:
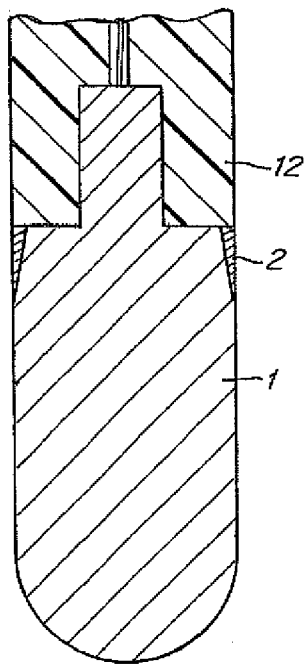
FIG. 1 illustrates a cross-sectional side view of a prior art distal tip electrode.

This invention is not limited in its application to the details of construction and the arrangement of components and acts set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

While energy is supplied to an ablation electrode to heat surrounding tissue, some of the energy heats the electrode, and heat from the surrounding tissue and/or blood can also heat the electrode. The flow of blood at body temperature can help to remove heat from the electrode by cooling the electrode as it passes over the exposed electrode surface. If the rate of electrode heating exceeds the and the rate of electrode cooling, for example if the blood flow rate is low, the temperature of the electrode rises and may reach temperatures that cause blood coagulation. In some catheter systems, the highest temperatures in energized ablation electrodes may be found at the junction of the ablation electrode and the catheter.

Finite element analysis of ablation procedure models has revealed that localized hotspots can indeed occur at the junction of the electrode and the catheter. The abrupt change in electrical properties at the junction can lead to a current density concentration, resulting in increased electrode temperature and/or blood heating. To address this issue, prior art catheters have employed a transition zone between an electrode and a catheter. For example, referring to FIG. 1, the diameter of an electrode 1 is slightly tapered at the junction with a catheter shaft 12, and a conductive skirt 2 with a tapered thickness provides graduated electrical properties and maintains the outer surface of the device flush with the outer surface of the catheter 12. U.S. Pat. No. 5,257,635 is one example of such a catheter.

As described above, while performing ablation procedures, excessive electrode temperatures can lead to undesirable blood coagulation. Embodiments of the present invention are directed to a junction of an ablation electrode and a catheter that reduces temperature hotspots in an ablation electrode. In one embodiment, a channel is provided at the junction of the ablation electrode and the catheter. In other embodiments, the junction of the ablation electrode and an insulating material is configured such that the two materials meet to form a steep angle.

System Overview

Figure 2:
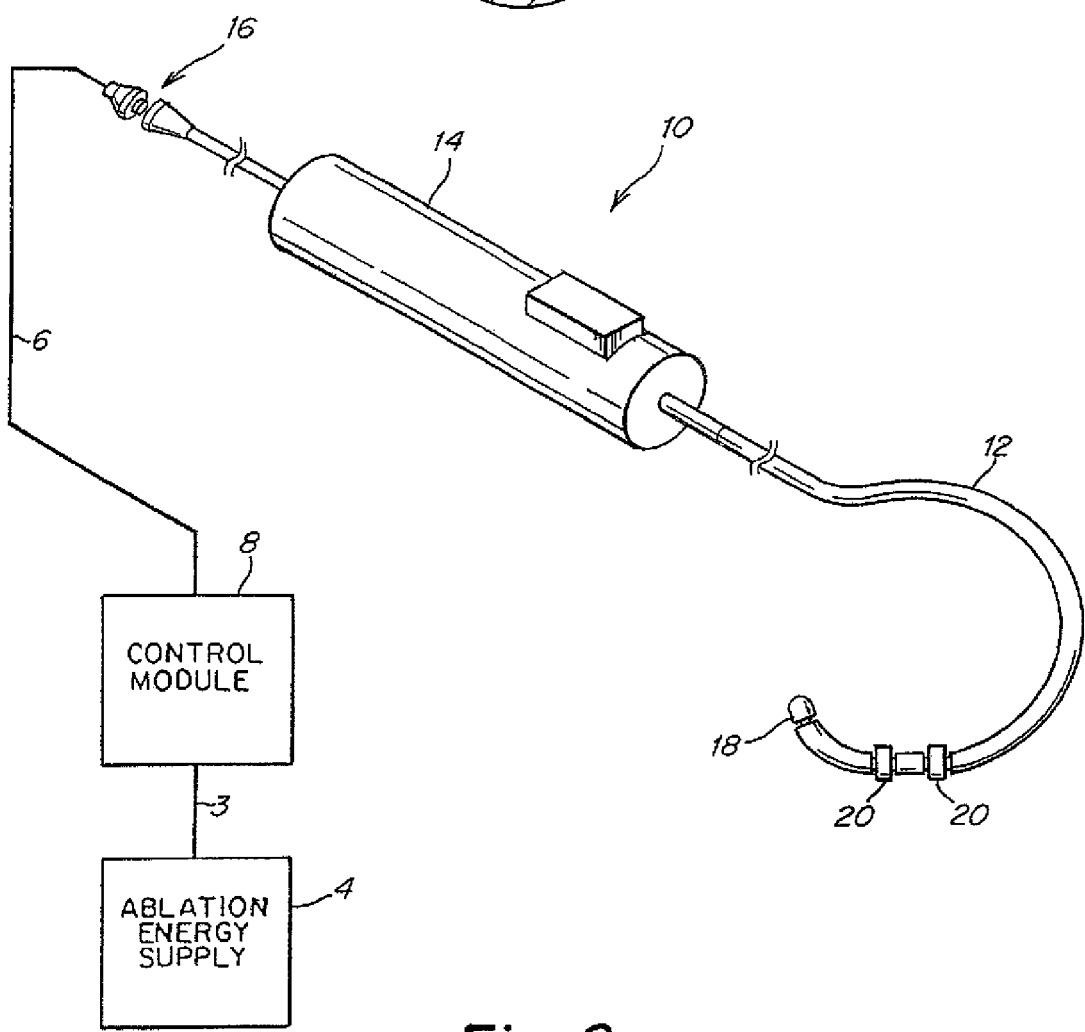
FIG. 2 illustrates a catheter system according to embodiments of the present invention.

Reference is now made to FIG. 2, which figure illustrates an overview of an ablation catheter system in accordance with embodiments of the present invention. The system includes a catheter 10 having a shaft portion 12, a control handle 14, and a connector portion 16. A control module 8 is connected to connector portion 16 via cable 6. Ablation energy supply 4 may be connected to control module 8 via cable 3. Control module 8 is used to control ablation energy provided by ablation energy supply 4 to catheter 10. Although illustrated as separate devices, ablation energy supply 4 and control module 8 may be incorporated into a single device.

In this description, various aspects and features of embodiments of the present invention will be described. The various features of the embodiments of the invention are discussed separately for clarity. One skilled in the art will appreciate that the features may be selectively combined in a device depending upon the particular application. Furthermore, any of the various features may be incorporated in a catheter and associated methods of use for ablation procedures.

Catheter Overview

Still referring to FIG. 2, catheter 10 may include a distal tip electrode 18 and/or one or more ring electrodes 20. Electrodes 18, 20 may be arranged on shaft 12 such that portions of their outer surfaces have the same diameter as the catheter shaft, or they may be arranged such that the electrode outer surfaces have diameters that are larger or smaller than the shaft diameter. In some embodiments, electrodes 18, 20 may be adjustable in size or shape, have an eccentric shape, or may be mounted eccentrically on shaft 12. In some embodiments, electrodes 18, 20 may be approximately four millimeters in length.

Distal tip electrode 18 may be affixed to the distal tip of shaft 12 in such a manner as to not move relative to the distal tip, or distal tip electrode 18 may be moveable relative to shaft 12. Catheter 10 may be a steerable device. FIG. 2 illustrates the distal tip portion 18 being deflected by the mechanism contained within control handle 14. Control handle 14 may include a rotatable thumb wheel (not shown) which can be used by a user to deflect the distal end of the catheter. The thumb wheel (or any other suitable actuating device) is connected to one or more pull wires which extend through shaft portion 12 and are connected to the distal end 18 of the catheter at an off-axis location, whereby tension applied to one or more of the pull wires causes the distal portion of the catheter to curve in a predetermined direction or directions.

An ablation energy supply 4 is provided to supply the electrode(s) with energy in the form of, for example, RF, microwave, DC, ultrasound, or laser radiation.

Control module 8 controls the energy supplied to the electrode(s) by regulating various energy supply parameters. For example, for some ablation procedures, control module 8 may supply energy to the electrodes 18, 20 until a set electrode temperature is reached, at which time the energy supply may be reduced to maintain the electrodes 18, 20 at or below a predetermined temperature. In other embodiments, control module 8 may sustain the supplied energy at a constant power, a constant voltage or a constant current. In other ablation procedures, control module 8 may vary any of the above parameters or control other parameters such as frequency, pulse rate, amplitude, duty cycle, wave shape, or any other suitable parameters.

Junction

Figure 3:
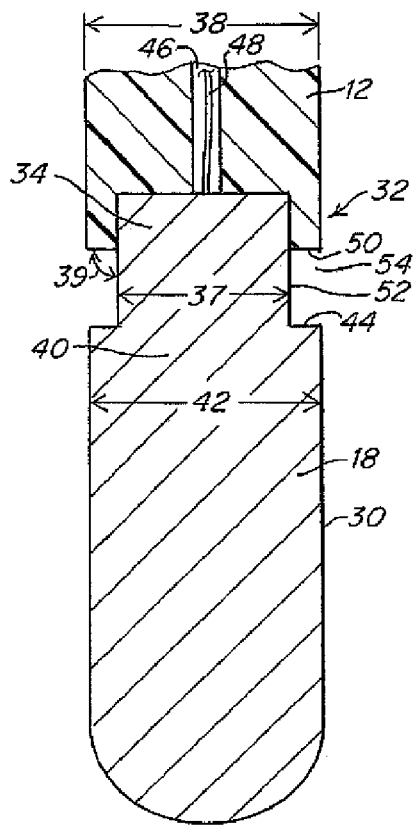
FIG. 3 illustrates a cross-sectional side view of a distal tip electrode according to one embodiment of the invention.

Referring now to FIG. 3, a distal tip electrode 18 according to one embodiment of the invention is illustrated. Electrode 18 has an exposed surface 30 for transmitting energy to tissue to form lesions. Electrode 18 is attached to a catheter shaft 12 at a junction 32. In the illustrated embodiment, electrode 18 has an attachment portion 34 that is insertable into shaft 12. The method of attachment of electrode 18 to shaft 12 is not intended to be limiting, and any suitable method may be used.

At an area near junction 32, electrode 18 includes a first diameter portion 36 with a diameter 37 that is smaller than a shaft diameter 38. First diameter portion 36 forms an angle 39 with shaft 12 that is a substantially right angle. Away from junction 32, in the direction of the distal end of electrode 18, electrode 18 includes a second diameter portion 40 with a diameter 42 that is larger than the diameter 37 of first diameter portion 36. A transition face 44 is formed at the transition of first diameter portion 36 and second diameter portion 40. The diameter of second diameter portion 40 is illustrated to be the same as the shaft diameter 38 in this embodiment, however, in other embodiments, second diameter portion 40 may have a diameter that is either larger or smaller than shaft diameter 38. In some embodiments, second diameter portion 40 may have a diameter toward its proximal end that is smaller than shaft diameter 38 and have a diameter that is larger than shaft diameter 38 toward its distal end. For purposes herein, the existence of a diameter for an electrode or other element does not require that the element be circular.

By providing a first diameter portion 36 that intersects with shaft 12 away from the outer surface of shaft 12, a first sidewall 50 is created. Transition face 44 provides another sidewall and the exposed electrode surface along first diameter portion 36 becomes a base 52 of a channel 54. In one illustrative embodiment, channel 54 has a base that extends approximately 0.9 mm from the catheter junction 32 to the second diameter portion 40.

Exposed electrode surface 30 is configured to contact either tissue or a blood flow. The distal end of electrode 18 may be slightly embedded in tissue, held at a tissue surface, or positioned a certain distance from the tissue surface in the blood flow. Junction 32 is configured such that transition face 44 and base 54 are exposed surfaces, that is, surfaces across which blood is able to flow during typical ablation procedures. If channel 54 is too narrow to allow adequate blood flow, unheated blood does not flow through the channel to remove heat from the electrode, and any blood that does enter channel 54 may stagnate and be heated to a coagulation temperature. In one embodiment, base 52 is at least 0.3 mm wide to allow blood to flow across the channel surfaces. In another embodiment, base 54 has a width of at least 10% of a largest diameter of the electrode.

In the illustrated embodiment, channel 54 encircles the electrode. As will be evident to one of skill in the art, channel 54 could extend partially or substantially around the circumference of electrode 18 without completely encircling the electrode. In some embodiments, several channel portions may extend around portions of the circumference of electrode 18 with non-channel portions intermediate the channels.

Recessed regions other than the illustrated channels may be used to provide a gap between insulating material and transition face 44. For example, a plurality of recessed regions that extend further in the longitudinal direction of the electrode than in the circumferential direction may be employed to provide gaps between insulating material and a second diameter portion.

Base 52, first sidewall 50 and transition face 44 do not necessarily have to be flat or smooth. Ridges, dimples, bumps, cavities, projections, fins or other surface features may be present on the various surfaces forming channel 54.

Large widths of channel base 52 may detract from the effectiveness of electrode 18 by reducing the surface area of electrode 18. In some embodiments, base 52 has a width no larger than the diameter 37 of first diameter portion 36.

Shaft 12 includes a longitudinally extending lumen 46 through which an electrical lead 48 passes. Electrical lead 48 is electrically connected to ablation energy supply 4 and attached at its distal end to insertion portion 34 of electrode 18 for supplying energy to electrode 18. The method of supplying energy to electrode 18 is not intended to be limiting and any suitable method may be used.

Additional electrically insulating material (not shown) may be disposed between electrode 18 and shaft 12 and still be considered to be part of shaft 12. In this manner, for purposes herein, an electrode that forms an angle with an electrically insulating material attached to the shaft, or attached to shaft insulating material, is considered to be forming an angle with the shaft or with shaft insulating material.

Figure 4:
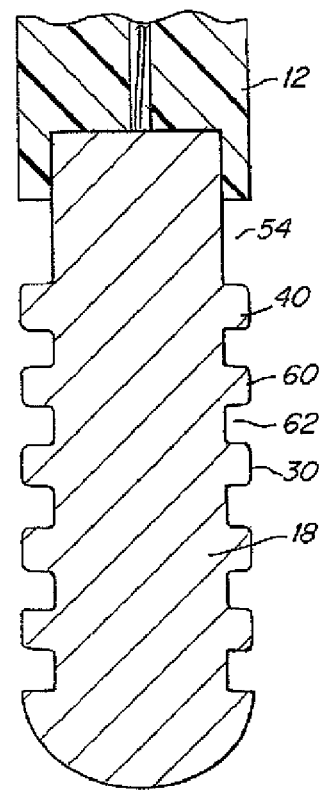
FIG. 4 illustrates a cross-sectional side view of a distal tip electrode according to another embodiment of the invention.

Various electrode features may also be included on distal tip electrode 18, as shown in the illustrative embodiment of FIG. 4. In addition to channel 54, the electrode shown in FIG. 4 includes projections 60 and channels 62 formed within exposed surface 30 of the electrode. The projections 60 and channels 62 may help with convective cooling of electrode 18 by providing a larger surface area over which blood may flow.

In any of the embodiments described herein, an active electrode cooling system (not shown) may be employed. In an active electrode cooling system, a fluid is passed through the interior of the electrode to draw heat away from the electrode. An active electrode cooling system is not required, but its use may be combined with passive cooling characteristics of electrodes, and the electrodes may be configured to accommodate the active electrode cooling systems.

Figure 5:
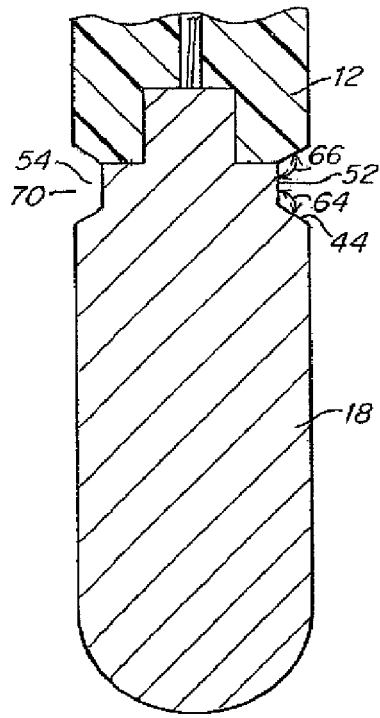
FIG. 5 illustrates a cross-sectional side view of a distal tip electrode according to a further embodiment of the invention.

As shown in the illustrative embodiment of FIG. 5, the sidewalls of the channel 54 do not necessarily have to intersect the base at 90° angles. For example, transition face 44 may form an angle 64 with base 52 of approximately 120°. Similarly, base 52 may intersect with shaft 12 to form an angle 66 of approximately 120°. In such an embodiment, the channel has a top opening 70 that is wider than base 52. In other embodiments, opening 70 may be more narrow than base 52. In such embodiments, the sidewalls of channel 54 may form angles of less than 90° with base 52.

Figure 6:
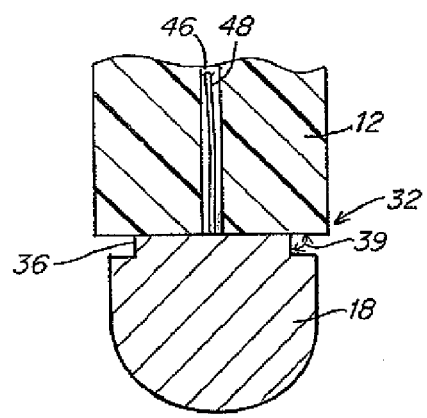
FIG. 6 illustrates a cross-sectional site view of a distal tip electrode according to another embodiment of the invention.

Electrode 18 does not need to be inserted into catheter shaft 12 to form a junction with shaft 12. For example, as illustrated in FIG. 6, electrode 18 can be attached to the distal end of shaft 12 without any insertion into shaft 12. In this embodiment, first diameter portion 36 forms junction 32 with shaft 12 by meeting shaft 12 at an angle 39 of approximately 90°. Electrical lead 48 passes through lumen 46 and is attached to electrode 18 at the proximal end of first diameter portion 36.

Figure 7:
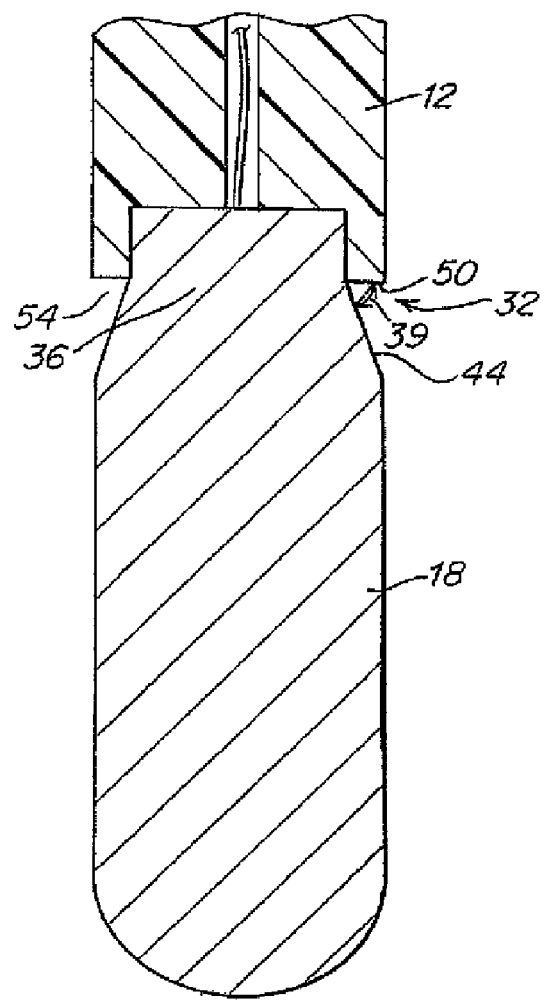
FIG. 7 illustrates a cross-sectional site view of a distal tip electrode according to a further embodiment of the invention.

FIG. 7 illustrates an embodiment in which transition face 44 and first sidewall 50 form channel 54 at junction 32 of electrode 18 and shaft 12. In this embodiment, transition face 44 forms both the base and the sidewall of channel 54, and forms an angle 39 of less than 90° with shaft 12. In some embodiments, transition face 44 may form an angle 39 of approximately 60° with shaft 12.

Figure 8:
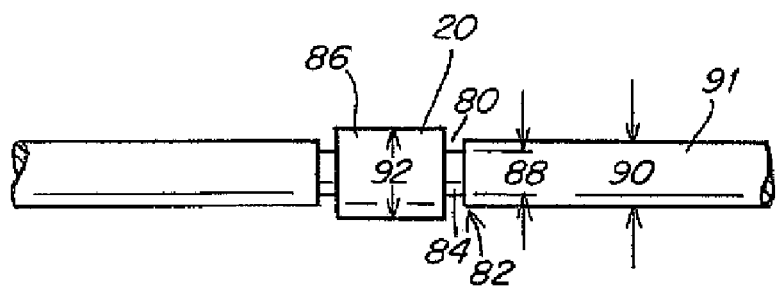
FIG. 8 illustrates a side view of a ring electrode according to a another embodiment of the invention.

The use of channels or other recessed regions at the junction of an electrode and a catheter is not limited to distal tip electrodes. In embodiments such as the one shown in FIG. 8, a ring electrode 20 may include a channel 80 at an electrode-catheter junction 82. Ring electrode 20 has a first diameter portion 84 and a second diameter portion 86. As can be seen in FIG. 8, first diameter portion 84 has a diameter 88 that is smaller than diameter 90 of shaft 91, and second diameter portion 86 has a diameter 92 that is larger than shaft diameter 90. Similar to the embodiments of FIGS. 2-5, the diameter of second diameter portion 86 may be smaller or the same as shaft diameter 90. Other modifications, such as projections, cavities, ridges, etc., for example, may be employed with ring electrode 20. Solid electrodes or hollow electrodes may be used with various embodiments disclosed herein.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A catheter comprising:
   a catheter shaft having a distal end, the distal end of the catheter shaft having an insulating material and a diameter; and
   an ablation electrode forming a junction with the distal end of the shaft, the ablation electrode having an exposed surface;
   wherein, extending from the junction, the exposed electrode surface has a first diameter portion with a first diameter that is smaller than the diameter of the distal end of the shaft, the first diameter portion forming an angle with the insulating material; and
   wherein the exposed electrode surface has a second diameter portion with a second diameter that is larger than the first diameter of the first diameter portion, the second diameter portion having a largest diameter that is smaller than a length of the second diameter portion; and
   wherein the exposed electrode surface further comprises a transition face extending from the first diameter portion to the second diameter portion, the transition face forming an approximately ninety degree angle with the first diameter portion; and
   wherein the insulating material, the first diameter portion and the transition face form a recessed region that allows blood to flow across the first diameter portion and the transition face when the electrode is placed in a blood flow.

2. The catheter according to claim 1, wherein the ablation electrode further comprises a plurality of recessed regions that allow blood to flow across exposed surfaces of the recessed regions when the electrode is placed in a blood flow.

3. The catheter according to claim 1, wherein the ablation electrode is a distal tip ablation electrode.

4. The catheter according to claim 1, wherein the transition face forms an approximately ninety degree angle with the exposed surface of the second diameter portion.

5. The catheter according to claim 1, wherein the distance from the insulating material to the transition face along the first diameter portion is at least 0.3 millimeters.

6. The catheter according to claim 1, wherein the distance from the insulating material to the transition face along the first diameter portion is less than the diameter of the first diameter portion.

7. The catheter according to claim 1, wherein the distance from the insulating material to the transition face along the first diameter portion is approximately 0.9 millimeters.

8. The catheter according to claim 1, wherein the transition face extends at least 0.3 millimeters toward a center longitudinal axis of the electrode from the exposed surface of the electrode.

9. The catheter according to claim 1, wherein the recessed region encircles the ablation electrode.

10. The catheter according to claim 1, wherein a largest diameter of the electrode is no larger than a diameter of the insulating material forming the first sidewall.

11. The catheter according to claim 1, wherein the transition face is parallel to a distal end of the catheter shaft.

12. The catheter according to claim 1, wherein the first diameter portion and the insulating material form an angle of approximately ninety degrees.

13. The catheter according to claim 1, wherein the first diameter portion and the insulating material form an angle of more than ninety degrees.

14. The catheter according to claim 1, wherein the first diameter portion and the insulating material form an angle less than ninety degrees.

15. The catheter according to claim 1, wherein the ablation electrode is approximately four millimeters in length.

16. The catheter according to claim 1, further comprising an abrupt change in electrical properties at the junction of the ablation electrode and the distal end of the shaft.

17. A catheter comprising:
a shaft including an electrically insulating material; and
an ablation electrode forming a junction with the insulating material and having an exposed surface that forms a channel with the insulating material, the insulating material having a diameter at the junction;
wherein:
a base of the channel comprises a first diameter portion of the exposed electrode surface, and the first diameter portion has a diameter that is smaller than the diameter of the insulating material at the junction;
a first sidewall of the channel comprises the insulating material at the junction;
a second sidewall of the channel comprises a transition face between the first diameter portion and a second diameter portion of the electrode;
the exposed electrode surface of the first diameter portion is parallel to the second diameter portion of the electrode; and
a length of the second diameter portion of the electrode is greater than a diameter of the second diameter portion; and
the channel is sized to allow blood to flow across the channel base and the second sidewall when the electrode is placed in a blood flow.

18. The catheter according to claim 17, wherein the second sidewall forms an angle of less than 120 degrees with the channel base.

19. The catheter according to claim 17, wherein the ablation electrode further comprises a plurality of channels that allow blood to flow across exposed surfaces of the channels when the electrode is placed in a blood flow.

20. The catheter according to claim 17, wherein the ablation electrode is a distal tip ablation electrode.

21. The catheter according to claim 17, wherein the ablation electrode is a ring ablation electrode.

22. The catheter according to claim 17, wherein the second sidewall forms an approximately ninety degree angle with the channel base.

23. The catheter according to claim 17, wherein the distance from the first sidewall to the second sidewall along the base is at least 0.3 millimeters.

24. The catheter according to claim 17, wherein the distance from the first sidewall to the second sidewall along the base is less than a diameter of the first diameter portion.

25. The catheter according to claim 17, wherein the second sidewall extends at least 0.3 millimeters toward a center longitudinal axis of the electrode from an outer surface of the electrode.

26. The catheter according to claim 17, wherein the channel encircles the ablation electrode.

27. The catheter according to claim 17, wherein a largest diameter of the electrode is no larger than a diameter of the insulating material forming the first sidewall.

28. The catheter according to claim 17, wherein the ablation electrode is approximately four millimeters in length.

29. The catheter according to claim 17, further comprising an abrupt change in electrical properties at the junction formed by the ablation electrode with the insulating material.

30. A catheter comprising:
a catheter having an insulating sheath; and
an ablation electrode non-moveably attached to the insulating sheath, forming a junction with an end of the insulating sheath, and forming a channel with the end of insulating sheath;
wherein:
the end of the insulating sheath has a diameter;
a base of the channel comprises an exposed electrode surface of the ablation electrode, and a diameter of the ablation electrode along the channel base is smaller than the diameter of the end of the insulating sheath;
a first sidewall of the channel comprises the end of the insulating sheath, and the channel base intersects the end of the insulating sheath;
a second sidewall of the channel comprises an exposed electrode surface which extends from the channel base to a portion of the ablation electrode which has a diameter that is larger than the diameter of the channel base portion;
the channel base is parallel to the larger diameter portion of the electrode; and
a width of the base of channel is at least one-tenth of the size of the largest diameter of the electrode and less than the smallest diameter of the electrode.

31. The catheter according to claim 30, wherein the electrode is a distal tip electrode.

32. The catheter according to claim 30, wherein the electrode is a ring electrode.

33. The catheter according to claim 30, further comprising an abrupt change in electrical properties at the junction formed by the ablation electrode with the insulating material.

34. A method of manufacturing a catheter tip, comprising:
providing a catheter shaft with an insulating sheath;
providing an ablation electrode having a first diameter portion with an exposed surface, a second diameter portion with an exposed surface, a transition face between the first and second diameter portions, and the second diameter portion having a length that is larger than a largest diameter of the second diameter portion; and
attaching the electrode to the shaft such that:
the first diameter portion of the electrode forms a junction with the insulating sheath, and the first diameter portion has a diameter that is smaller than a diameter of the insulating sheath at the junction of the electrode and the shaft;
each of the transition face and the sheath forms a sidewall of a channel and the first diameter portion of the electrode forms a base of the channel;
the insulating sheath, the first diameter portion and the transition face form a recessed region that is sized to allow blood to flow across the first diameter portion and the transition face when the electrode is placed in a blood flow; and
the transition face forms an approximately ninety degree angle with the channel base.

35. The method according to claim 34, wherein attaching the electrode to the shaft results in the base of channel being at least 0.9 millimeters wide from sidewall to sidewall.

36. The method according to claim 34, wherein attaching the electrode to the shaft comprises forming an abrupt change in electrical properties at the junction of the electrode with the insulating sheath.

* * * * *